(12) United States Patent
Palmer

(10) Patent No.: US 10,118,072 B2
(45) Date of Patent: Nov. 6, 2018

(54) SMART PEDAL FOR CYCLE STYLE EXERCISE DEVICES

(71) Applicant: Robin B. Palmer, Woodland Hills, CA (US)

(72) Inventor: Robin B. Palmer, Woodland Hills, CA (US)

(*) Notice: Subject to any disclaimer, the term of this patent is extended or adjusted under 35 U.S.C. 154(b) by 0 days.

(21) Appl. No.: 15/864,761

(22) Filed: Jan. 8, 2018

(65) Prior Publication Data

US 2018/0126220 A1  May 10, 2018

Related U.S. Application Data

(63) Continuation-in-part of application No. 15/177,008, filed on Jun. 8, 2016, now Pat. No. 9,889,335.

(51) Int. Cl.
| | |
|---|---|
| A63B 24/00 | (2006.01) |
| A63B 71/06 | (2006.01) |
| A63B 21/00 | (2006.01) |
| A63B 23/04 | (2006.01) |
| H04W 4/80 | (2018.01) |

(Continued)

(52) U.S. Cl.
CPC .... *A63B 24/0062* (2013.01); *A63B 21/00069* (2013.01); *A63B 21/4034* (2015.10); *A63B 21/4049* (2015.10); *A63B 23/0476* (2013.01); *A63B 71/0622* (2013.01); *A63B 22/0605* (2013.01); *A63B 2022/0097* (2013.01); *A63B 2022/0652* (2013.01); *A63B 2071/0658* (2013.01); *A63B 2209/00* (2013.01); *A63B 2210/50* (2013.01); *A63B 2220/40* (2013.01); *A63B 2220/62* (2013.01); *A63B 2220/803* (2013.01); *A63B 2225/50* (2013.01); *A63B 2230/75* (2013.01); *H04W 4/80* (2018.02)

(58) Field of Classification Search
CPC .......... A63B 21/00069; A63B 21/4034; A63B 21/4049; A63B 22/0046; A63B 22/06; A63B 22/0605; A63B 22/0611; A63B 2022/0097; A63B 23/0476; A63B 69/16; A63B 2208/0228; A63B 2208/0233; A63B 2208/0238; A63B 2210/00; A63B 2210/50; A63B 2225/09; B62K 2207/00; B62K 2207/02; B62K 2207/04
See application file for complete search history.

(56) References Cited

U.S. PATENT DOCUMENTS

| | | | | |
|---|---|---|---|---|
| 2011/0059825 | A1* | 3/2011 | McGown | A63B 24/0062 482/1 |
| 2011/0082009 | A1* | 4/2011 | Ranky | A63B 22/0605 482/8 |

(Continued)

*Primary Examiner* — Joshua Lee
(74) *Attorney, Agent, or Firm* — Bond Schoeneck & King, PLLC; David Nocilly; George McGuire

(57) ABSTRACT

A pedal system for tracking use of a cycle style exercise device. The pedal system includes a pedal with a shaft for coupling to the pedal crank of the exercise device and a housing that is rotatable about the shaft. An accelerometer positioned in the housing is configured to provide data about the movement of the pedal to a microcontroller. A wireless communication chip positioned in the housing is used to transmit the data about the movement of the pedal to a remote device via the wireless communication chip. The remote device is programmed to receive, display and track the data about the movement of the pedal.

7 Claims, 8 Drawing Sheets

(51) Int. Cl.
　　　*A63B 22/00*　　　(2006.01)
　　　*A63B 22/06*　　　(2006.01)

(56) References Cited

U.S. PATENT DOCUMENTS

| | | | |
|---|---|---|---|
| 2014/0259705 A1* | 9/2014 | Stevovich | B62M 3/08 33/1 N |
| 2014/0297070 A1* | 10/2014 | Gros | B62M 6/50 701/22 |
| 2015/0158549 A1* | 6/2015 | Gros | B62M 3/08 74/594.4 |
| 2016/0052583 A1* | 2/2016 | Sasaki | B62J 99/00 74/594.4 |

* cited by examiner

SMART PEDAL FOR CYCLE STYLE EXERCISE DEVICES

CROSS-REFERENCE TO RELATED APPLICATION

The present application is a continuation-in-part of U.S. application Ser. No. 15/177,008 filed Jun. 8, 2016.

BACKGROUND OF THE INVENTION

1. Field of the Invention

The present invention relates to exercise devices and, more particularly, to an internet enabled pedal that can be used with cycle style exercisers including bicycles.

2. Description of the Related Art

Most Americans sit over 9 hours a day, causing health problems like weight gain, back pain, heart disease and diabetes. Adding insult to injury, studies from Mayo Clinic, Blue Zones and Harvard show you lose 20 minutes of life for every hour you just sit there. Bicycles and other cycle style exercise equipment, including stationary cycles, are one of the most popular ways for users to engage in fitness activities to combat these problems. Recently advancements in cycle style exercise devices, such as the fold-flat, portable exerciser disclosed in U.S. Ser. No. 15/340,044, have improved the ease by which users can engage in exercise activities whether at home, at the office, at the gym, or even on an airplane. As many users have become familiar with fitness tracking products and associated mobile applications, there is a need in the art for a way to monitor and track the use of cycle style equipment, including fold flat cycles.

BRIEF SUMMARY OF THE INVENTION

The present invention is pedal system for monitoring the use of a cycle style device that includes a smart pedal that can monitor use of the cycle and communicate with a host application for managing and tracking usage over time. The pedal system has a shaft, a housing that is rotatable about the shaft, an accelerometer positioned in the housing and configured to provide data about the movement of the pedal, a microcontroller positioned in the housing and coupled to the accelerometer, and a wireless communication chip positioned in the housing and coupled to the microcontroller. The microcontroller is programmed to receive the data about the movement of the pedal from the accelerometer and to transmit the data about the movement of the pedal to a remote device via the wireless communication chip. The remotely positioned computing device is programmed to display and track the data received from the microcontroller via the wireless communication chip.

BRIEF DESCRIPTION OF THE SEVERAL VIEWS OF THE DRAWING(S)

The present invention will be more fully understood and appreciated by reading the following Detailed Description in conjunction with the accompanying drawings, in which.

DETAILED DESCRIPTION OF THE INVENTION

Figure 1:
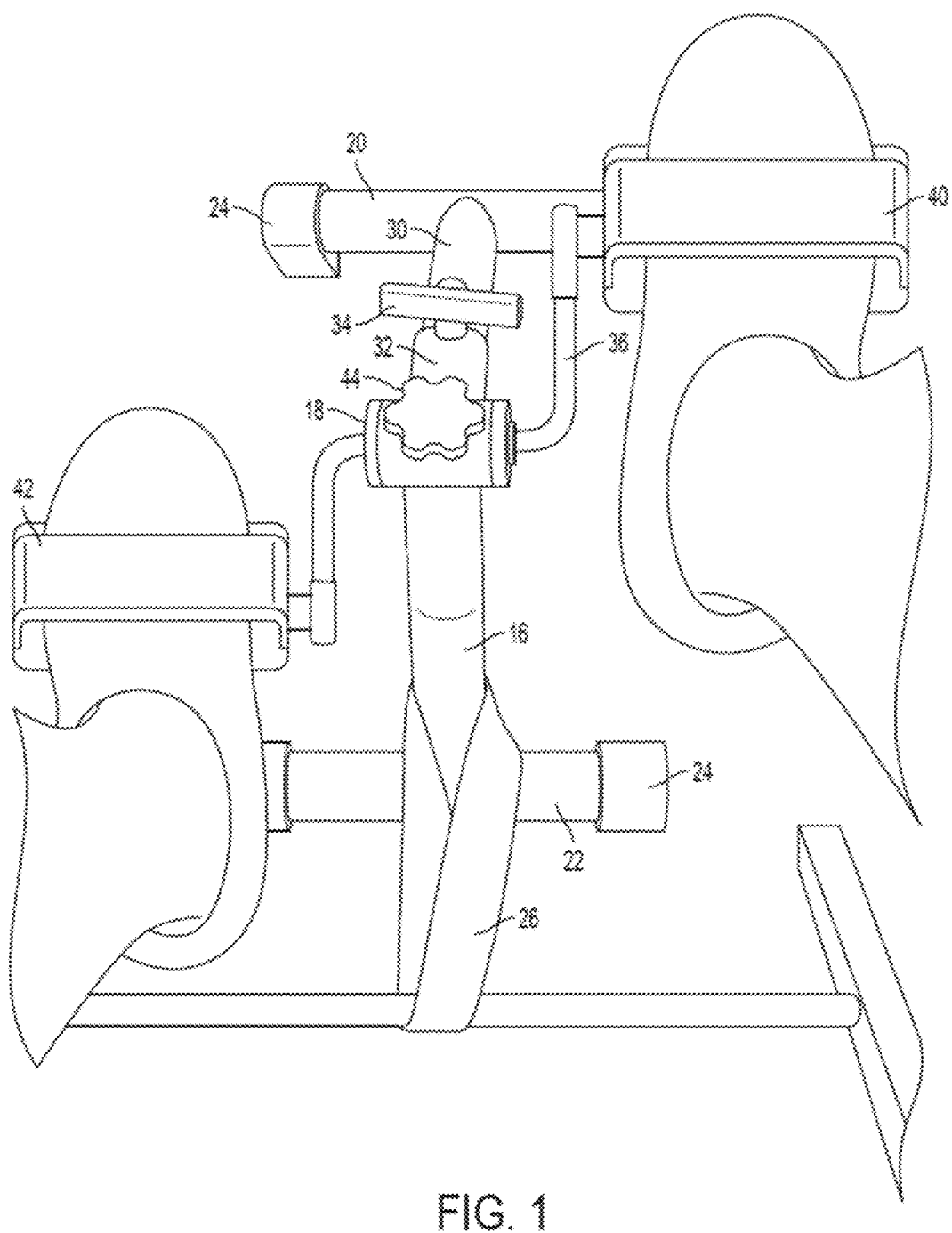
FIG. 1 is a top plan of an exercise device that may be outfitted with a pedal system according to the present invention.

Referring to the figures, wherein like numeral refer to like parts throughout, there is seen in FIG. 1, an exercise device 10 comprising a base 12 formed from two opposing struts 14 and 16 that are interconnected to each other by an axle housing 18 and extend outwardly. Outward ends of struts 14 and 16 include cross-members 20 and 22 that define two pairs of legs for secure engagement with a planar surface, such as a floor. The ends of the legs formed by cross-members 20 and 22 may be capped with resilient caps 24 to increase frictional contact with the planar surface upon which exercise device is placed. Struts 14 and 16 as well as cross-members 20 and 22 are preferably tubular to maximize strength while minimizing weight, and may be manufactured from high strength polymers or light weight metals and metal alloys for the same reason. A strap 26 may be coupled to base 12 to allow exercise 10 to be attached to an external structure, such as an airplane seat, to restrict movement of exercise device 10 when in use.

Figure 2:
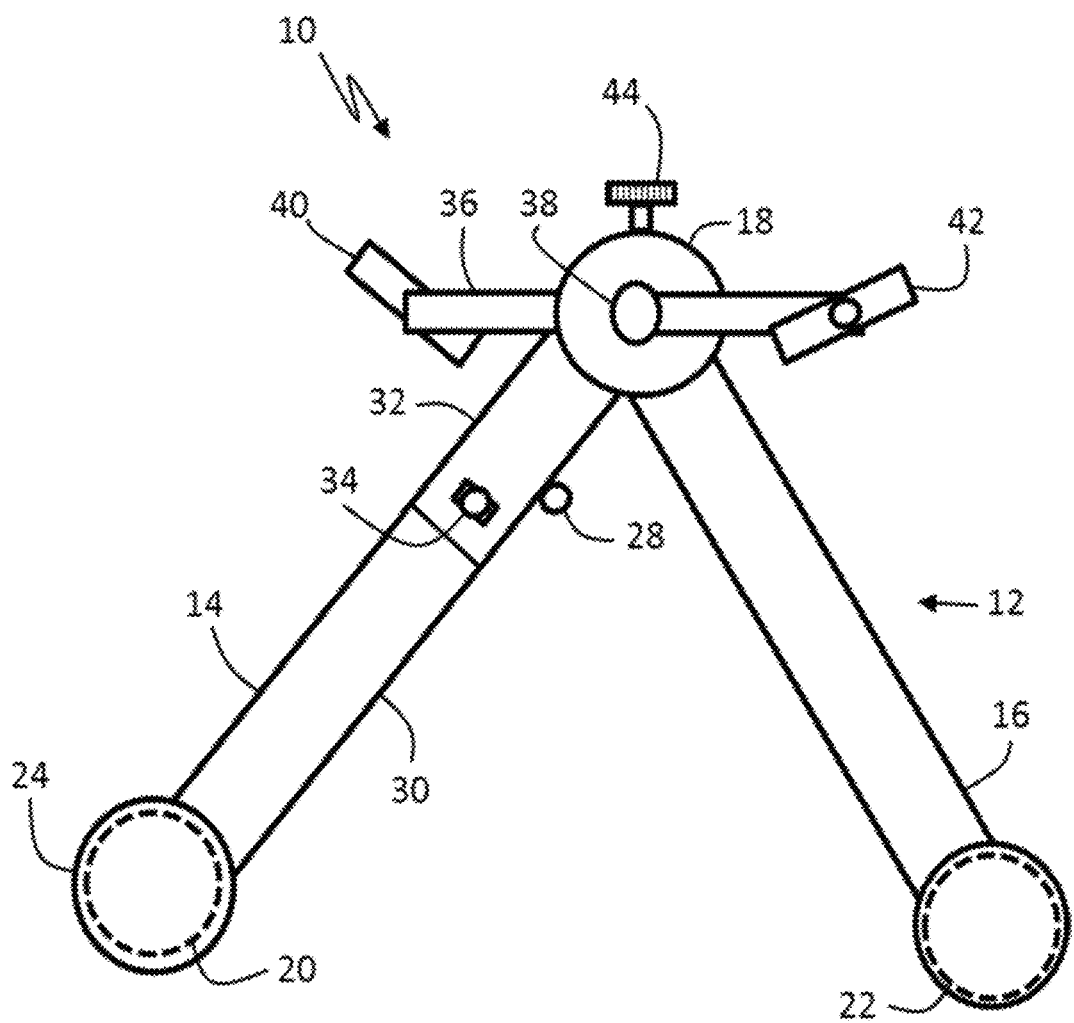
FIG. 2 is a side view of an exercise device that may be outfitted with a pedal system according to the present invention.
Figure 3:
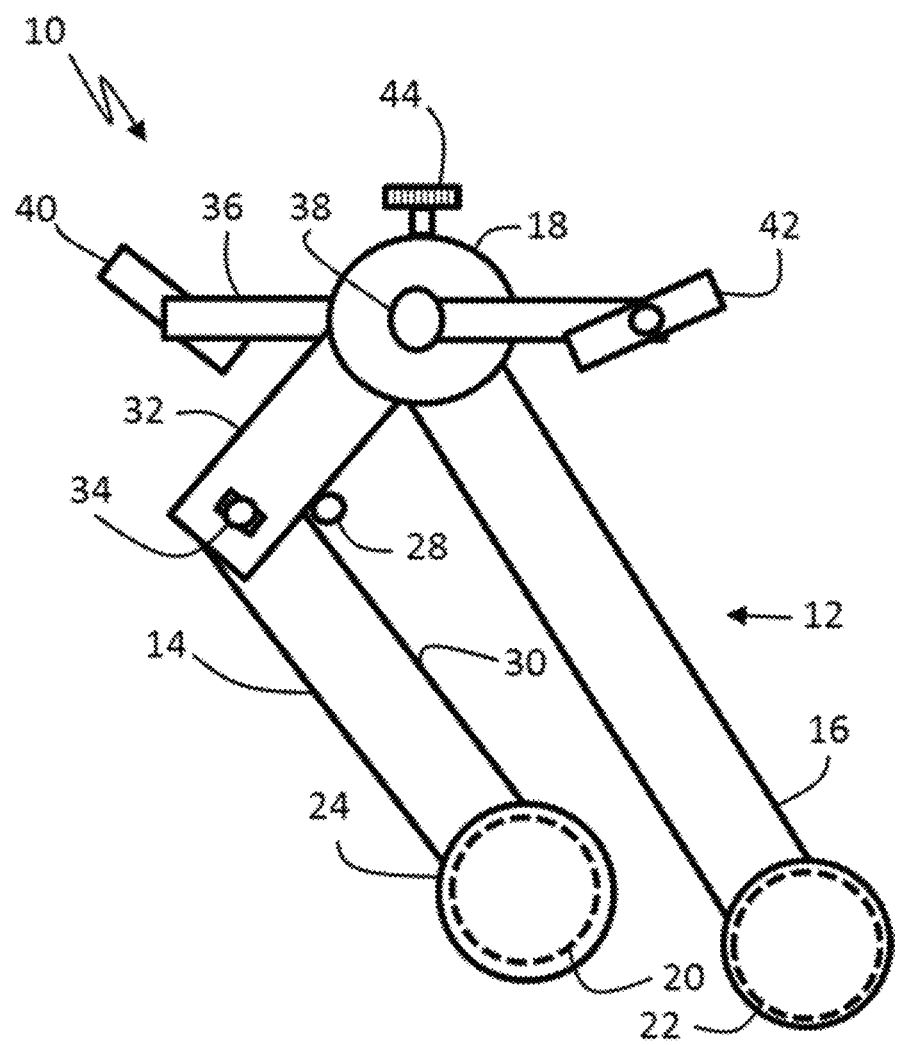
FIG. 3 is another side view of view of an exercise device that may be outfitted with a pedal system according to the present invention.

Strut 14 includes a hinge 28 dividing strut 14 into first and second segments 30 and 32. As seen in FIGS. 2 and 3, hinge 28 allows segments 30 and 32 to move between a first, collapsed configuration and a second, extended configuration. Hinge 28 further includes a locking member 34 that may be engaged and disengaged to selectively lock and unlock segments 30 and 32 in their extended configuration and, optionally, the collapsed configurations.

Axle housing 18 supports a pedal crank 36 having an axle 38 extending through axle housing 18 to position user pedals 40 and 42 on opposite sides of axle housing 18. As is known in the art, pedal crank 36 may be supported in axle housing 18 by a sealed bearing or similar structure for smooth rotation within axle housing 18. A tensioner 44 may be coupled to axle housing 18 to allow a user to change the amount of force needed to turn pedal crank 36. User pedals 40 and 42 are pivotally mounted to pedal crank 36 for movement between a folded position where pedals 40 and 42 are centrally stowed, and an unfolded position where pedals 40 and 42 are positioned so that a user can place their feet on pedals 40 and 42 to operate pedal crank 36 when exercise device 10 is placed on the floor in front of user, such as on the floor of an airplane in front of a passenger seat.

In one embodiment, exercise device 10 may be dimensioned so that it is 10 inches in width, 9.5 inches in height, and 15 inches in length and thus will fit within the standard floor space in the coach section of an airplane (approximately 17 inches in length and width). Collapsing strut 14 and folding pedals 40 and 42 inwardly will reduce the dimensions to just 5 inches in width, 12 inches in height, and 15 inches in length. As a result, exercise device 10 can be easily carried on and/or stored on an airplane in the collapsed configuration, and then unfolded and placed on the floor of the airplane for use. Using tensioner 44, a user may establish a comfortable amount of resistance and proceed to perform exercises that will increase blood flow and reduce the risk of thrombosis without having to leave the passenger seat. After exercise, device 10 may be collapsed and stowed.

Figure 4:
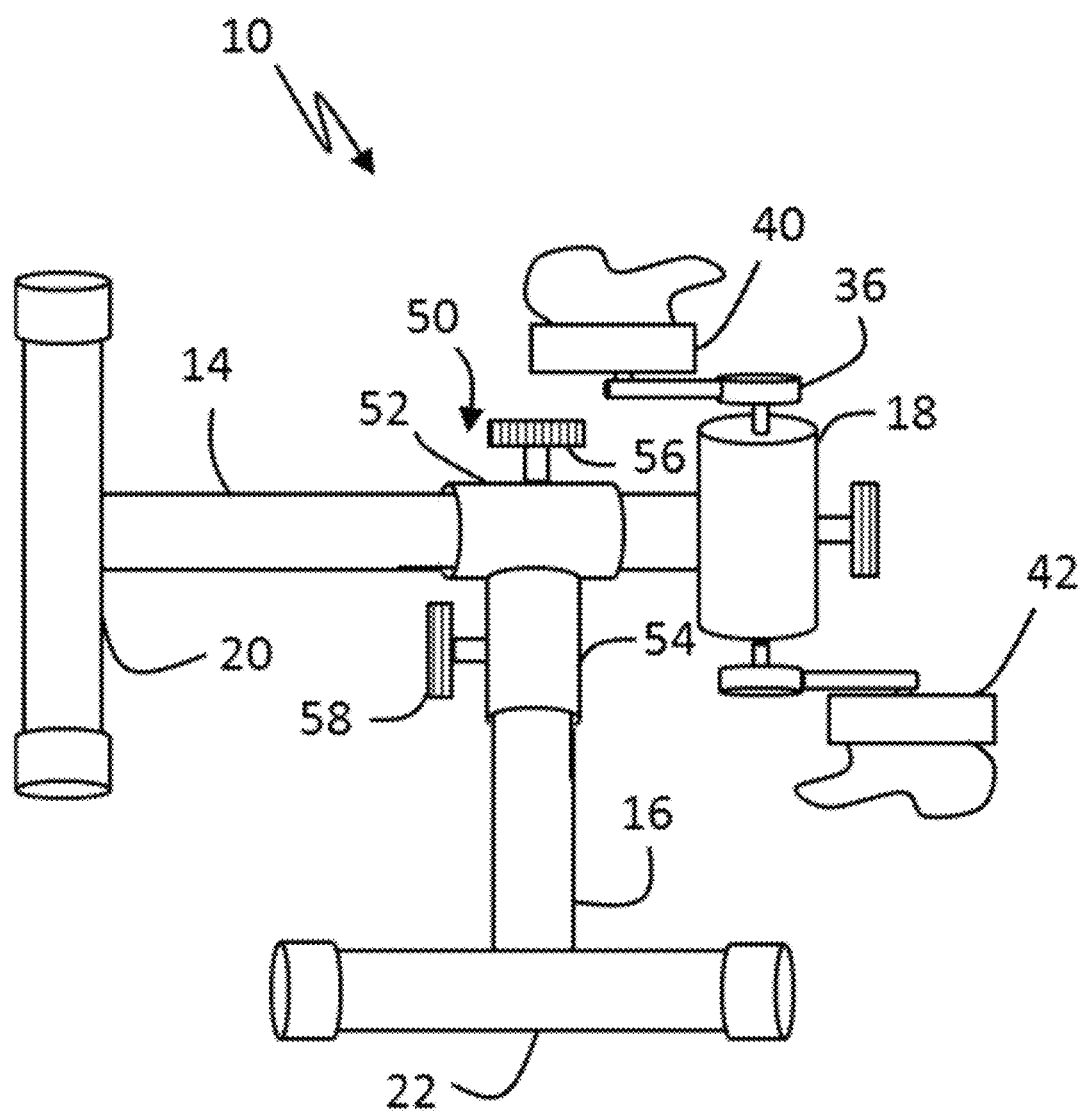
FIG. 4 is a top plan of an exercise device that may be outfitted with a pedal system according to the present invention.

Referring to FIG. 4, hinge 28 of exercise device 10 may be substituted with a coupling 50 that allows for rotation of struts 14 and 16 relative to each other so that exercise device 10 may be positioned into a substantially planar configuration. More specifically, coupling 50 comprises two strut engaging tubes 52 and 54 positioned at right angles to each other. Each of tubes 52 and 54 have manually adjustable clamps 56 and 58 associated therewith for selectively fixing and releasing struts 14 and 16 therein. As seen in FIG. 4, releasing struts 14 and 16 allows rotation of struts 14 and 16 relative to each other so that exercise device 10 may be folded flat into a substantially planar configuration. It should be recognized that this configuration may allow for each storage or transportation of device 10 in certain locations where a planar configuration is more advantageous, e.g., in a briefcase, under a seat, etc.

Figure 5:
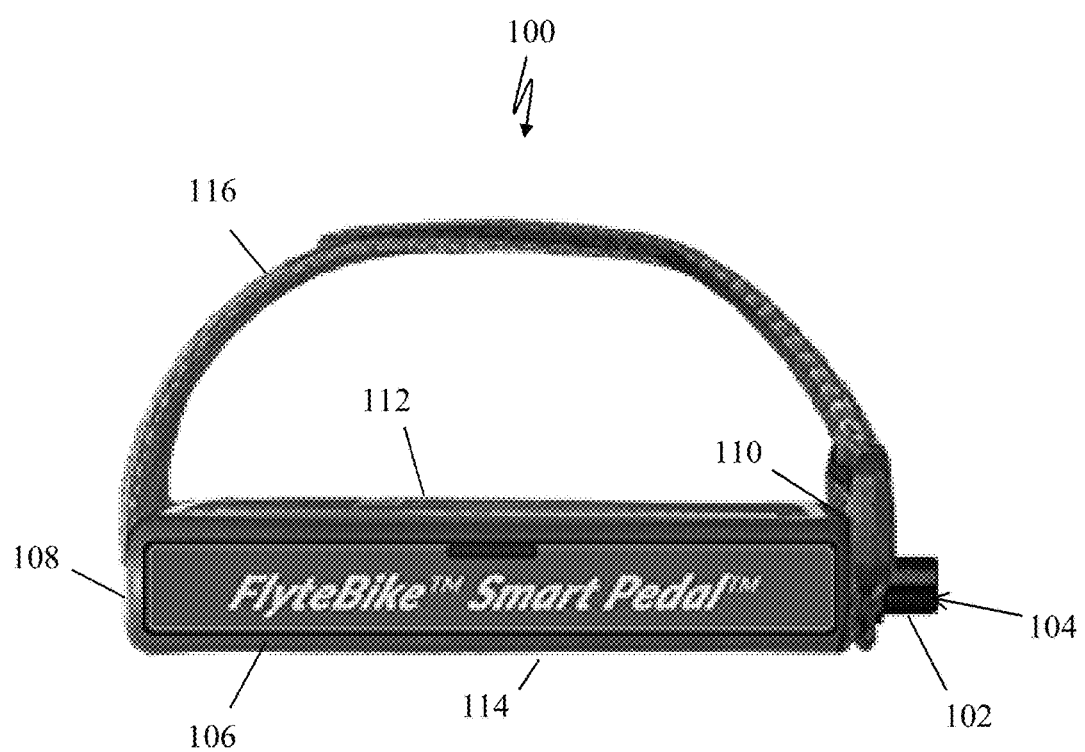
FIG. 5 is a schematic of a pedal system for an exercise an exercise device according to the present invention.

Referring to FIG. 5, one of user pedals 40 and 42 on opposite sides of axle housing 18 may comprise a smart pedal 100 according to the present invention. Smart pedal comprises a shaft 102 having a throughbore 104 that is dimensioned to accept and frictionally engage or be locked onto one of the ends of pedal crank 36. Alternatively, shaft 102 may include a post fixed therein that has a threaded end for attachment to corresponding threads on the end of pedal crank 36. Shaft 102 is coupled at both ends to a housing 106 by a pair of bearings 108 and 110 that allow shaft 102 to freely rotate relative to housing 106. Housing 106 is generally planar and has upper and lower surfaces 112 and 114 that are dimensioned to engage the foot of a user. Upper and lower surfaces 112 and 114 may include texturing to improve frictional engagement with the foot of a user, and housing 106 may include a foot strap 116 that assists in keeping the foot of the user in contact with housing 106.

Figure 6:
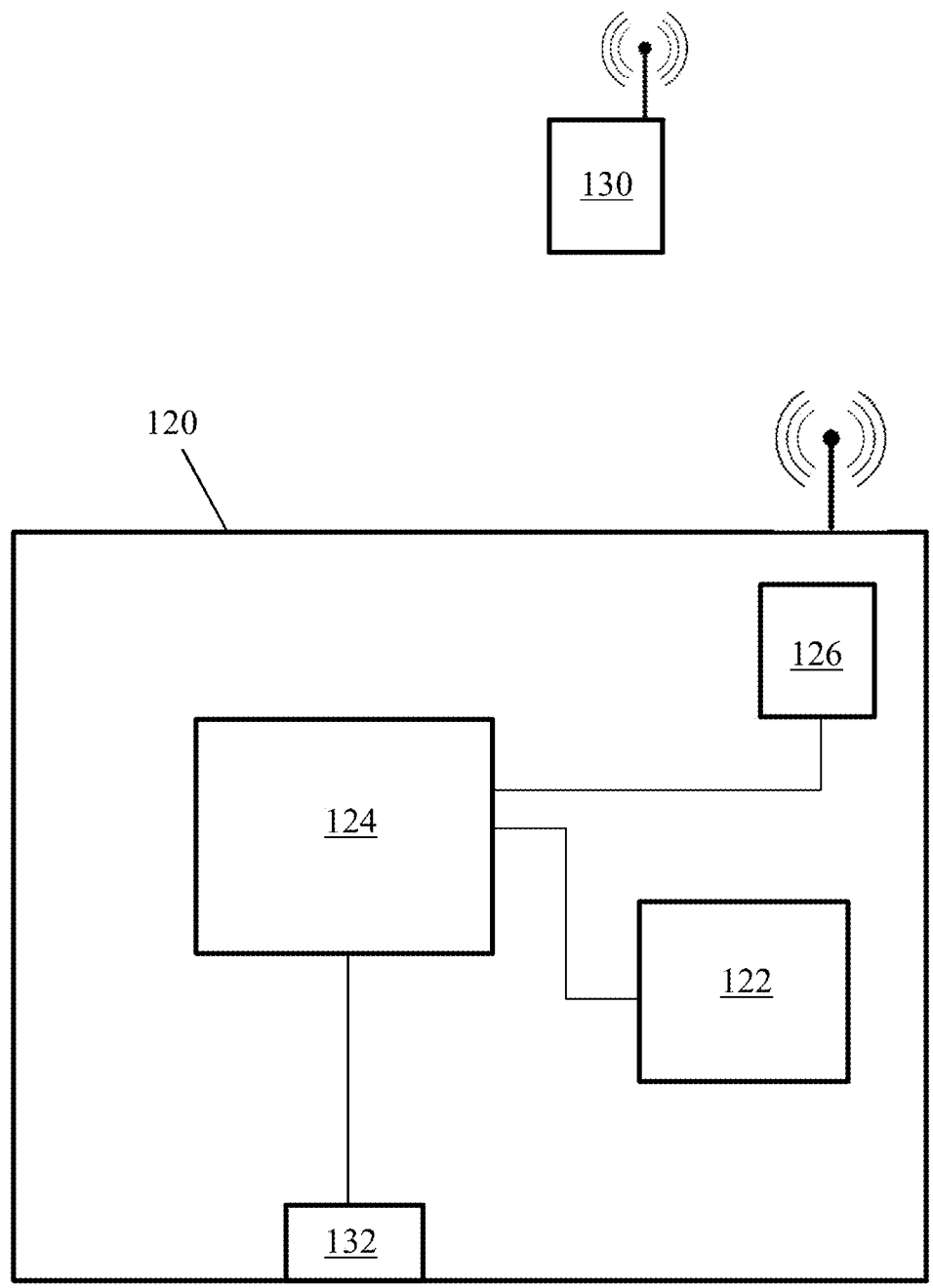
FIG. 6 is a schematic of an electronics package for a pedal system according to the present invention.

Referring to FIG. 6, housing 106 encloses an electronics assembly 120 for detecting and measuring the movement of smart pedal 100 such as when smart pedal 100 is attached to pedal crank 36 and driven by a user to turn pedal crank 36 and operate exercise device 10. For example, as seen in FIG. 6, electronics assembly 120 may include an accelerometer 122 such as a Model L3GD20HTR three-axis gyroscope available from ST Mems Gyroscopes. Electronics assembly 120 may further include a microcontroller 124, such as an Atmel Model ATSAMD21E17A-MU, that is coupled to accelerometer 122 and programmed to operate and collect data from accelerometer 122. Electronics assembly 120 may additionally include a wireless communication chip 126 coupled to microcontroller 124, such as a Microchip RN4871-V/RM118 compatible chip package or a low-power, high-performance chip adapted for 802.11 (2.4/5 GHz) connectivity, so that smart pedal 100 can engage in communications over a Bluetooth® connection or a Wi-Fi network with a remote device 130. Microcontroller 124 is thus programmed to prepare the data collected from accelerometer 122 for transmission to a remote device 130 and then transmit the data via a wireless communication chip 126. Electronics assembly 120 may also comprise a wires connection such as a USB port 132. It should be recognized by those of skill in the art that smart pedal 100 may include a standard power source, such as a battery, as well as conventional electronic components for managing sensors, regulating power, indicating status to a user, etc. and that the particular model of the various electronics components may be selected according to cost, performance, power usage, etc. as desired.

Figure 7:
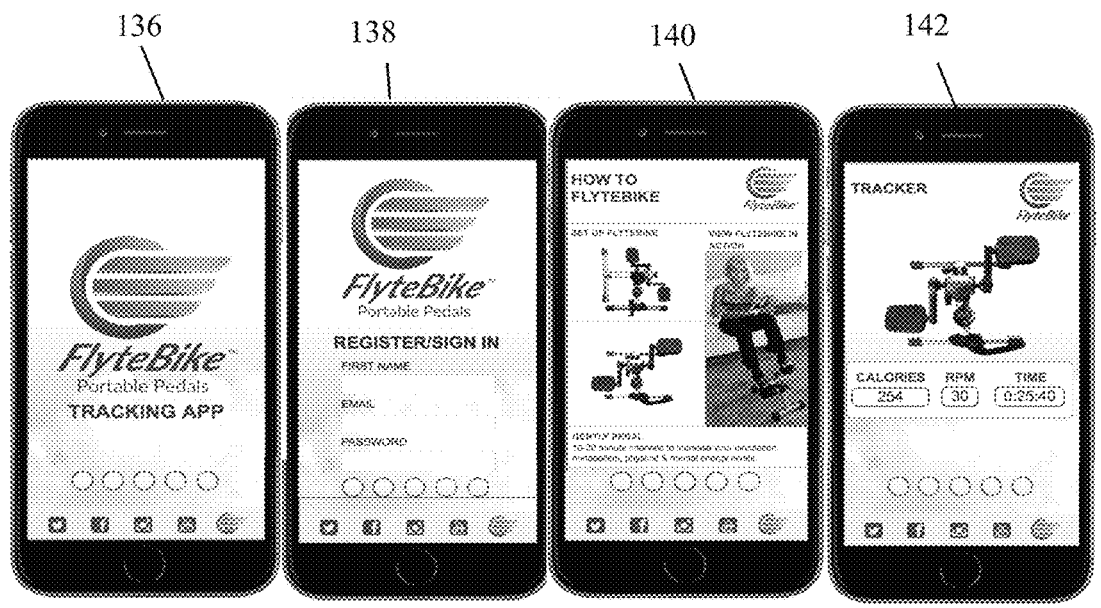
FIG. 7 is a schematic of a software application for a mobile device of a pedal system according to the present invention.
Figure 8:
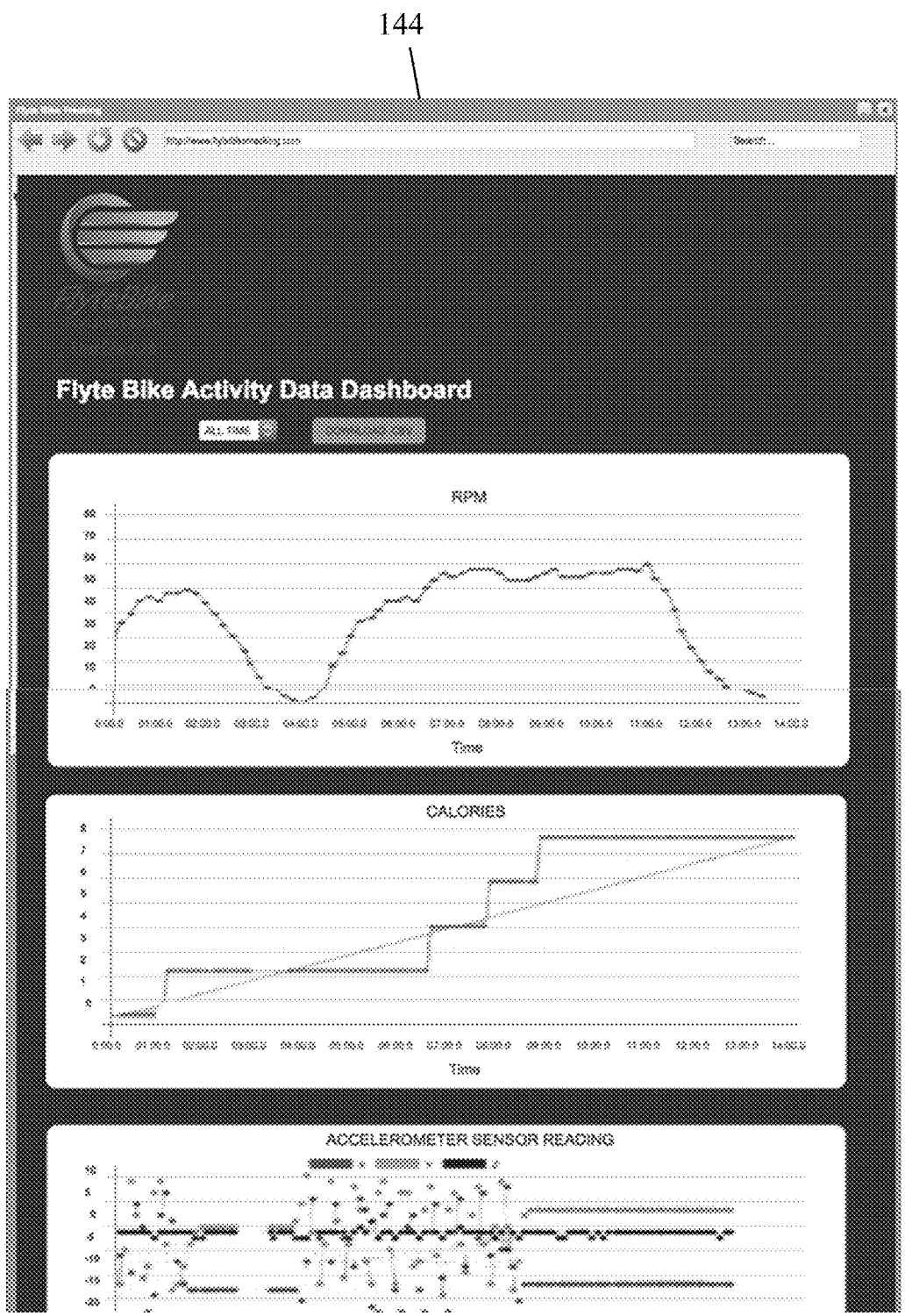
FIG. 8 is a schematic of an additional software application for a mobile device of a pedal system according to the present invention.

Smart pedal 100 is programmed to be in periodic communication with remote device 130, which may comprise a mobile phone, tablet, computer, or other receiver running an associated software application 136 for interpreting the sensor data collected and transmitted by smart pedal 100. As seen in FIG. 7, software application 136 may include a login screen 138 for security, instructional content 140, and general usage information 142 such as calories burned, pedaling rate, and elapsed time. As seen in FIG. 8, software application 136 may additionally include tracking modules 144 that can collect and display data about usage over time, such as RPM, calories burned, and accelerometer readings.

Although described in relation to exercise device 10, smart pedal 100 may be retrofitted onto an existing device that uses a pedal crank 36, such as a stationary bicycle, conventional bicycle, recumbent cycle, or any pedal exerciser.

As described above, the present invention may be a system, a method, and/or a computer program associated therewith and is described herein with reference to flowcharts and block diagrams of methods and systems. The flowchart and block diagrams illustrate the architecture, functionality, and operation of possible implementations of systems, methods, and computer programs of the present invention. It should be understood that each block of the flowcharts and block diagrams can be implemented by computer readable program instructions in software, firmware, or dedicated analog or digital circuits. These computer readable program instructions may be implemented on the processor of a general purpose computer, a special purpose computer, or other programmable data processing apparatus to produce a machine that implements a part or all of any of the blocks in the flowcharts and block diagrams. Each block in the flowchart or block diagrams may represent a module, segment, or portion of instructions, which comprises one or more executable instructions for implementing the specified logical functions. It should also be noted that each block of the block diagrams and flowchart illustrations, or combinations of blocks in the block diagrams and flowcharts, can be implemented by special purpose hardware-based systems that perform the specified functions or acts or carry out combinations of special purpose hardware and computer instructions.

What is claimed is:

1. A pedal system for a cycle, comprising:
   a shaft;
   a housing rotatable about the shaft;
   an accelerometer positioned in the housing and configured to provide data about any movement of the pedal;
   a microcontroller positioned in the housing and coupled to the accelerometer;
   a wireless communication chip positioned in the housing and coupled to the microcontroller; and
   wherein the microcontroller is programmed to receive the data about the movement of the pedal from the accelerometer and to transmit the data about the movement of the pedal system to a remote device via the wireless communication chip, wherein the pedal is mounted to a pedal crank supported by a crank housing and having a first strut that extends from the crank housing and a second strut that is interconnected to the first strut by a coupling that allows rotation of both of the first and second struts within the coupling and relative to each other so that the pedal system may be folded into a planar configuration.

2. The pedal system of claim 1, wherein the wireless communication chip is configured to transmit data via an 802.11 connection.

3. The pedal system of claim 1, wherein the wireless communication chip is configured to transmit data via a Bluetooth connection.

4. The pedal system of claim 1, further comprise a remotely positioned computing device in communication with the microcontroller via the wireless communication chip.

5. The pedal system of claim 4, wherein the remotely positioned computing device is programmed to display data received from the microcontroller via the wireless communication chip.

6. The pedal system of claim 4, wherein the remotely positioned computing device is programmed to track the data received from the microcontroller via the wireless communication chip over time.

7. The pedal system of claim 4, wherein the remotely positioned computing device is programmed to display the tracked data over time.

* * * * *